(12) United States Patent
Barnes et al.

(10) Patent No.: US 10,898,672 B2
(45) Date of Patent: Jan. 26, 2021

(54) MASK PRESSURE REGULATION IN CPAP TREATMENT AND ASSISTED RESPIRATION BY DYNAMIC CONTROL OF MASK VENT FLOW

(71) Applicant: ResMed Pty Ltd, Bella Vista (AU)

(72) Inventors: Adrian Barnes, Sydney (AU); John David Oates, Sydney (AU); Barton John Kenyon, Sydney (AU); Benriah Goeldi, Freiburg (DE)

(73) Assignee: ResMed Pty Ltd, Bella Vista (AU)

( * ) Notice: Subject to any disclaimer, the term of this patent is extended or adjusted under 35 U.S.C. 154(b) by 460 days.

(21) Appl. No.: 15/879,213

(22) Filed: Jan. 24, 2018

(65) Prior Publication Data

US 2018/0147385 A1 May 31, 2018

Related U.S. Application Data

(63) Continuation of application No. 11/887,537, filed as application No. PCT/AU2006/000418 on Mar. 29, 2006, now Pat. No. 9,901,703.
(Continued)

(51) Int. Cl.
*A61M 16/00* (2006.01)
*A61M 16/22* (2006.01)
(Continued)

(52) U.S. Cl.
CPC ........ *A61M 16/22* (2013.01); *A61M 16/0009* (2014.02); *A61M 16/0012* (2014.02); *A61M 16/024* (2017.08); *A61M 16/06* (2013.01); *A61M 16/0622* (2014.02); *A61M 16/0633* (2014.02); *A61M 16/0672* (2014.02); *A61M 16/0825* (2014.02); *A61M 16/0883* (2014.02); *A61M 16/202* (2014.02); *A61M 16/0066* (2013.01); *A61M 16/0093* (2014.02); *A61M 16/1055* (2013.01); *A61M 16/1065* (2014.02); *A61M 2016/0027* (2013.01); *A61M 2016/0039* (2013.01); *A61M 2206/14* (2013.01); *A61M 2230/432* (2013.01)

(58) Field of Classification Search
CPC .... A61M 16/00; A61M 16/20; A61M 16/201; A61M 16/203; A61M 16/204; A61M 16/205; A61M 16/208; A61M 16/209
See application file for complete search history.

(56) References Cited

U.S. PATENT DOCUMENTS 3,741,208 A 6/1973 Jonsson et al.
RE29,778 E * 9/1978 Stewart ................. A61M 16/00
128/204.24
(Continued)

OTHER PUBLICATIONS

Jun. 15, 2006 International Search Report issued in International Application No. PCT/AU2006/000418.

*Primary Examiner* — Michael J Tsai
(74) *Attorney, Agent, or Firm* — Nixon & Vanderhye P.C.

(57) ABSTRACT

An air delivery system includes an air flow generator to provide a pressurized flow of air, a patient interface to provide a seal with the patient's face in use, an air delivery conduit to interconnect the air flow generator and the patient interface, and a controllable vent valve to control venting from the patient interface. The vent valve is controlled to maintain a substantially constant air flow in the air delivery conduit and the air flow generator.

21 Claims, 4 Drawing Sheets

Related U.S. Application Data

(60) Provisional application No. 60/667,052, filed on Apr. 1, 2005, provisional application No. 60/706,430, filed on Aug. 9, 2005, provisional application No. 60/775,334, filed on Feb. 22, 2006.

(51) Int. Cl.
*A61M 16/08* (2006.01)
*A61M 16/06* (2006.01)
*A61M 16/20* (2006.01)
*A61M 16/10* (2006.01)

(56) References Cited

U.S. PATENT DOCUMENTS

| | | |
|---|---|---|
| 4,298,023 A * | 11/1981 | McGinnis ............ A61M 16/208 128/206.15 |
| 4,635,631 A | 1/1987 | Izumi |
| 5,161,525 A | 11/1992 | Kimm et al. |
| 5,540,219 A | 7/1996 | Mechlenburg et al. |
| 5,542,416 A * | 8/1996 | Chalvignac ....... A61M 16/0069 128/204.23 |
| 5,551,419 A | 9/1996 | Froehlich et al. |
| 5,598,838 A | 2/1997 | Servidio et al. |
| 5,694,923 A | 12/1997 | Hete et al. |
| 5,704,345 A | 1/1998 | Berthon-Jones |
| 5,865,173 A | 2/1999 | Froehlich |
| 5,906,203 A | 5/1999 | Klockseth et al. |
| 6,332,463 B1 | 12/2001 | Farrugia et al. |
| 6,363,933 B1 | 4/2002 | Berthon-Jones |
| 6,439,229 B1 | 8/2002 | Du et al. |
| 6,526,974 B1 | 3/2003 | Brydon et al. |
| 6,536,432 B2 | 3/2003 | Truschel |
| 6,745,770 B2 | 6/2004 | McAuliffe et al. |
| 6,752,150 B1 | 6/2004 | Remmers et al. |
| 2004/0107964 A1 * | 6/2004 | Shaw .................... A61M 16/00 128/203.22 |

\* cited by examiner

MASK PRESSURE REGULATION IN CPAP TREATMENT AND ASSISTED RESPIRATION BY DYNAMIC CONTROL OF MASK VENT FLOW

CROSS-REFERENCE TO APPLICATIONS

This application is a continuation of U.S. application Ser. No. 11/887,537, filed Feb. 10, 2011, which is the U.S. National Phase of International Application No. PCT/AU2006/000418, filed Mar. 29, 2006, which designates the U.S. and claims priority to Provisional Application Nos. 60/667,052, filed Apr. 1, 2005, 60/706,430, filed Aug. 9, 2005, and U.S. Pat. No. 60,775,334, filed Feb. 22, 2006, each incorporated by reference in its entirety.

FIELD OF THE INVENTION

The present invention relates to an air delivery system used for treatment, e.g., of sleep disordered breathing (SDB) such as obstructive sleep apnea (OSA).

BACKGROUND OF THE INVENTION

Patients who suffer from obstructive sleep apnea can use continuous positive airway pressure (CPAP) therapy to maintain the upper airway open while they are asleep. CPAP therapy is applied to the patient using a mask, tubing, and a flow generator. All of these components encompass the air delivery system provided to the patient.

One problem with CPAP therapy is that the flow impedance of a flow generator air delivery path results in pressure swings at the mask when the breathing load changes. As the impedance of the delivery path or the respiratory flow increases so will the observed pressure swings.

An existing solution to this problem includes reducing the inertia of the turbine or increasing peak power delivery from the power supply. These increase the ability of the system to compensate for changes in mask pressure. However, compensating for the pressure swings by adjusting the turbine pressure results in increased noise and bearing wear, and is fundamentally limited by the rate at which the turbine pressure can be changed, e.g., see U.S. Pat. No. 6,332,463.

Another existing solution to this problem includes constraining the product to have a low flow impedance delivery path, e.g., ResMed's S6 device. However, maintaining a low flow impedance of the delivery air path in a flow generator may compromise other product design goals, e.g., the turbine inlet air path being constrained to reduce radiated noise, the delivery hose being reduced in diameter, or a humidifier or filter being added to the patient circuit.

Under these conditions, it may be difficult to lower the pressure swings at the mask to clinically acceptable levels and therapy delivery may be compromised.

Thus, there is a need for an improved system that does not suffer from the above-mentioned drawbacks.

SUMMARY OF THE INVENTION

One aspect of the invention relates to methods or systems used to compensate for pressure swings at the entrance to the patient's airway induced by respiratory flow in the course of continuous positive airway pressure (CPAP) treatment or assisted respiration.

Another aspect of the invention relates to an air delivery system including an air flow generator to provide a pressurized flow of air, a patient interface to provide a seal with the patient's face in use, an air delivery conduit to interconnect the air flow generator and the patient interface, and a controllable vent valve to control venting from the patient interface. The vent valve is controlled to maintain a substantially constant air flow in the air delivery conduit and the air flow generator.

Another aspect of the invention relates to a method for delivering pressurized air to a patient. The method includes delivering pressurized air to a patient interface and controlling venting from the patient interface to maintain a substantially constant air flow in the air delivery conduit and the air flow generator.

Another aspect of the invention relates to a method for delivering pressurized air to a patient. The method includes delivering pressurized air to a patient interface and Controlling venting from the patient interface to maintain a substantially constant pressure at the patient interface.

Other, aspects, features, and advantages f this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

The air delivery methods or systems described below are alternatives to the methods described in U.S. Pat. No. 6,332,463 to ResMed Limited, the entirety incorporated herein by reference. In the illustrated embodiments described herein, the air delivery methods or systems eliminate the effect of delivery circuit impedance on mask pressure swings without requiring a dynamic adjustment of the turbine speed. Because the methods or systems described below are not restricted by physical response of a mechanical rotating element (i.e., a valve has a faster response time), they potentially allow the use of more restrictive air paths.

Aspects of the air delivery methods or systems described below may be incorporated into other systems such as the Ventless Mask CPAP System described in U.S. Patent Application No. 60/706,430, filed Aug. 9, 2005, the entirety incorporated herein by reference.

1. First Illustrated Embodiment of Air Delivery System

Figure 1:
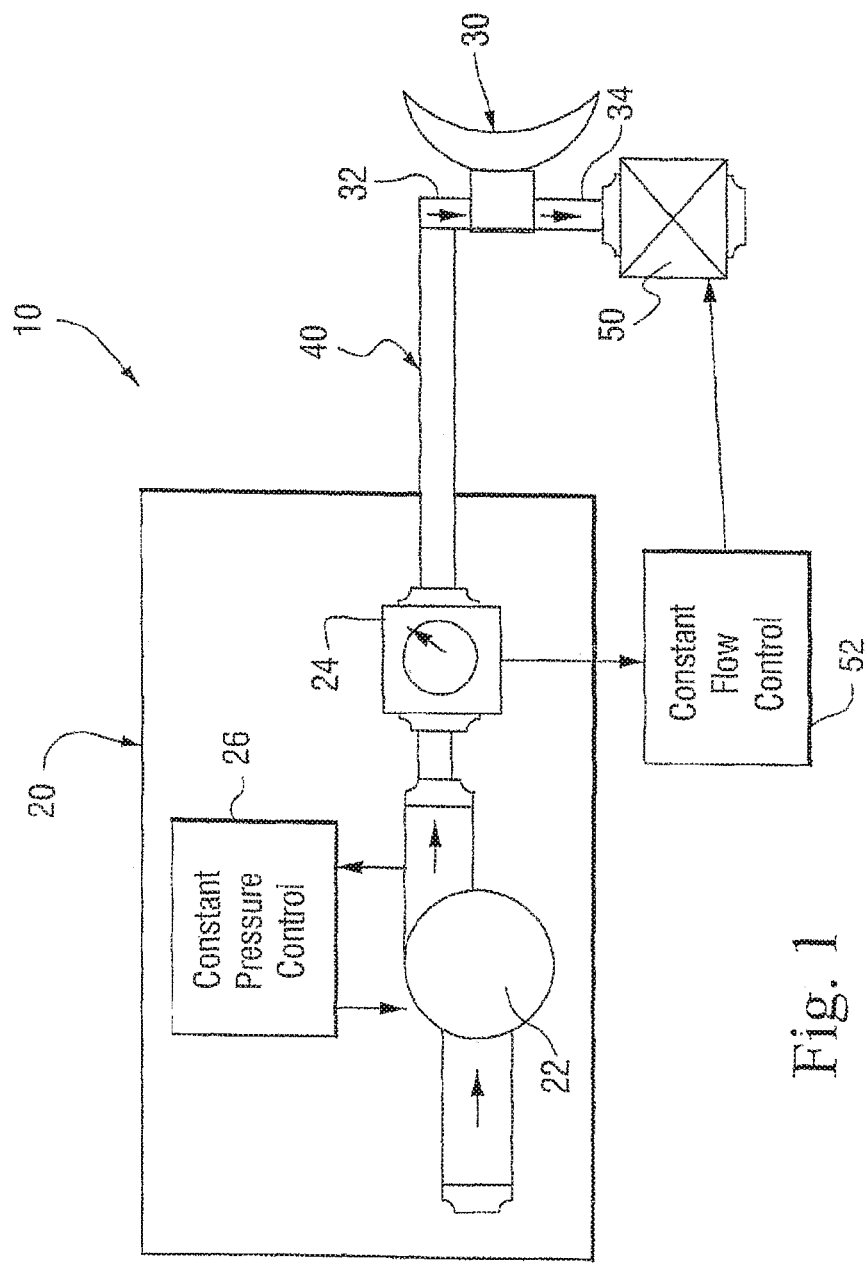
FIG. 1 is a schematic view of an air delivery system according to an embodiment of the present invention.

FIG. 1 illustrates an air delivery system 10 according to an embodiment of the present invention. The air delivery system 10 is structured to deliver a supply of pressurized breathable air to a patient for treatment, e.g., of Sleep Disordered Breathing (SDB) with CPAP or Non-Invasive Positive Pressure Ventilation (NIPPV).

As illustrated, the air delivery system 10 includes an air flow generator 20, a patient interface 30, e.g., mask, and an air delivery conduit 40.

The flow generator 20 includes an air turbine or blower 22 and a flow measuring element 24, e.g., a flow meter. The air turbine 22 is operable to draw a supply of air into the flow generator through one or more intake openings and provide a pressurized flow of air at an outlet. The air turbine 22 is driven by a controllable electric motor. The electric motor is controlled by a constant pressure control 26 so as to deliver constant elevated pressure ($P_{turbine}$) at constant flow ($F_{delivery}$). The constant pressure control 26 may be provided by a number of mechanisms including a constant rpm control or a feedback circuit incorporating a pressure transducer, for example. The flow measuring element 24 provides a representation of the air flow through the flow generator ($F_{delivery}$). In the illustrated embodiment, the flow measuring device 24 is provided at the outlet of the flow generator 20. However, the flow measuring device 24 may be located at any point in the air path of the flow generator 20, e.g., either before or after the air turbine 22.

The supply of pressurized air is delivered to the patient via the air delivery conduit 40 that includes one end communicated to the outlet of the flow generator 20 and an opposite end communicated to the patient interface 30. The air delivery conduit 40 may have any suitable construction, and may be communicated or coupled to the flow generator 20 and the patient interface 30 in any suitable manner. The pressure drop between the flow generator 20 and the patient interface 30 at constant flow may be characterized as ($P_{drop}$).

The patient interface 30 comfortably engages the patient's face and provides a seal so that pressurized air ($P_{mask}$) can be delivered to the patient. The patient interface 30 may have any suitable configuration as is known in the art, e.g., full-face mask, nasal mask, oro-nasal mask, mouth mask, nasal prongs, etc. The patient interface or mask 30 is equipped with two ports 32, 34. The first port 32 is an inlet port for the delivery of air (e.g., via air delivery conduit 40), and the second port 34 is an outlet port for the venting of exhaled air and surplus air flow. The patient air flow ($F_{patient}$) will consist of both respiratory air flow components ($F_{resp}$) and non-respiratory air flow components including mask leak ($F_{nonresp}$).

The vent flow ($F_{vent}$) from the outlet port 34 is controlled by a controllable proportional valve or vent valve 50 in such a manner so as to maintain a constant delivery flow ($F_{delivery}$) for all normal patient flow conditions. In the illustrated embodiment, the vent valve 50 is external to the flow generator 20. The vent flow ($F_{vent}$) is indirectly modulated by patient respiration, i.e., decreasing during inspiration and increasing during expiration.

The vent valve 50 is controlled by a constant flow control 52. The constant flow control 52 receives feedback from the flow measuring element 24 for ($F_{delivery}$) and selectively adjusts the vent valve 50 for ($F_{vent}$) to maintain constant flow.

1.1 Constant Regulation of Mask Pressure

The constant delivery flow is selected to be the maximum patient flow expected under normal conditions ($F_{delivery}=\max(F_{resp}+F_{nonresp})$). In one example, this would be 75 l/min.

The vent flow required to maintain this constant flow is given by ($F_{vent}=F_{delivery}-F_{resp}-F_{nonresp}$). In an embodiment, this would be in the range 0-125 l/min. The vent flow varies as the respiratory flow varies in order to maintain constant mask pressure. Thus, if the mask pressure is constant and the flow generator pressure is constant, then the inlet flow would also be constant.

The mask pressure is a function of the turbine pressure and the pressure drop in the air delivery conduit ($P_{mask}=P_{turbine}-P_{drop}$). At constant flow, the turbine pressure and the pressure drop are constant, and so the air delivery system 10 provides a constant, regulation of mask pressure.

1.2 Control Algorithm

Figure 2:
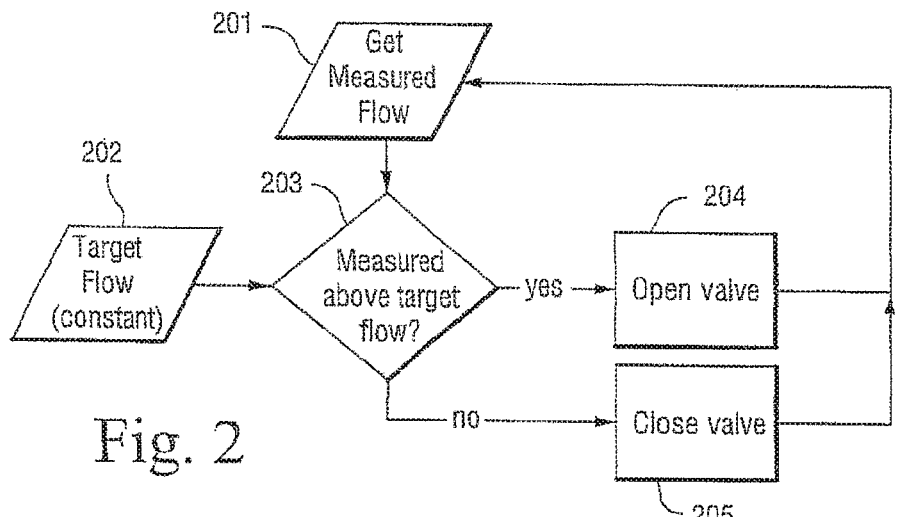
FIG. 2 is an embodiment of a control algorithm for the air delivery systems shown in FIGS. 1 and 3.

FIG. 2 illustrates a control algorithm for the air delivery system 10 of FIG. 1. The algorithm is preferably implemented using software, although hardware implementations are also possible. As illustrated, the measured air flow is obtained from the flow measuring element 24 at step 201. A target air flow, i.e., constant air flow, is established at step 202, and the measured air flow is compared to the target air flow at step 203. If the measured air flow is above the target air flow, then the vent valve 50 is opened further via control 52 at step 204. If the measured air flow is not above the target air flow, then the vent valve 50 is adjusted towards the closed position via control 52 at step 205. The process continues through operation of the air delivery system 10 to maintain constant flow.

2. Second Illustrated Embodiment of Air Delivery System

Figure 3:
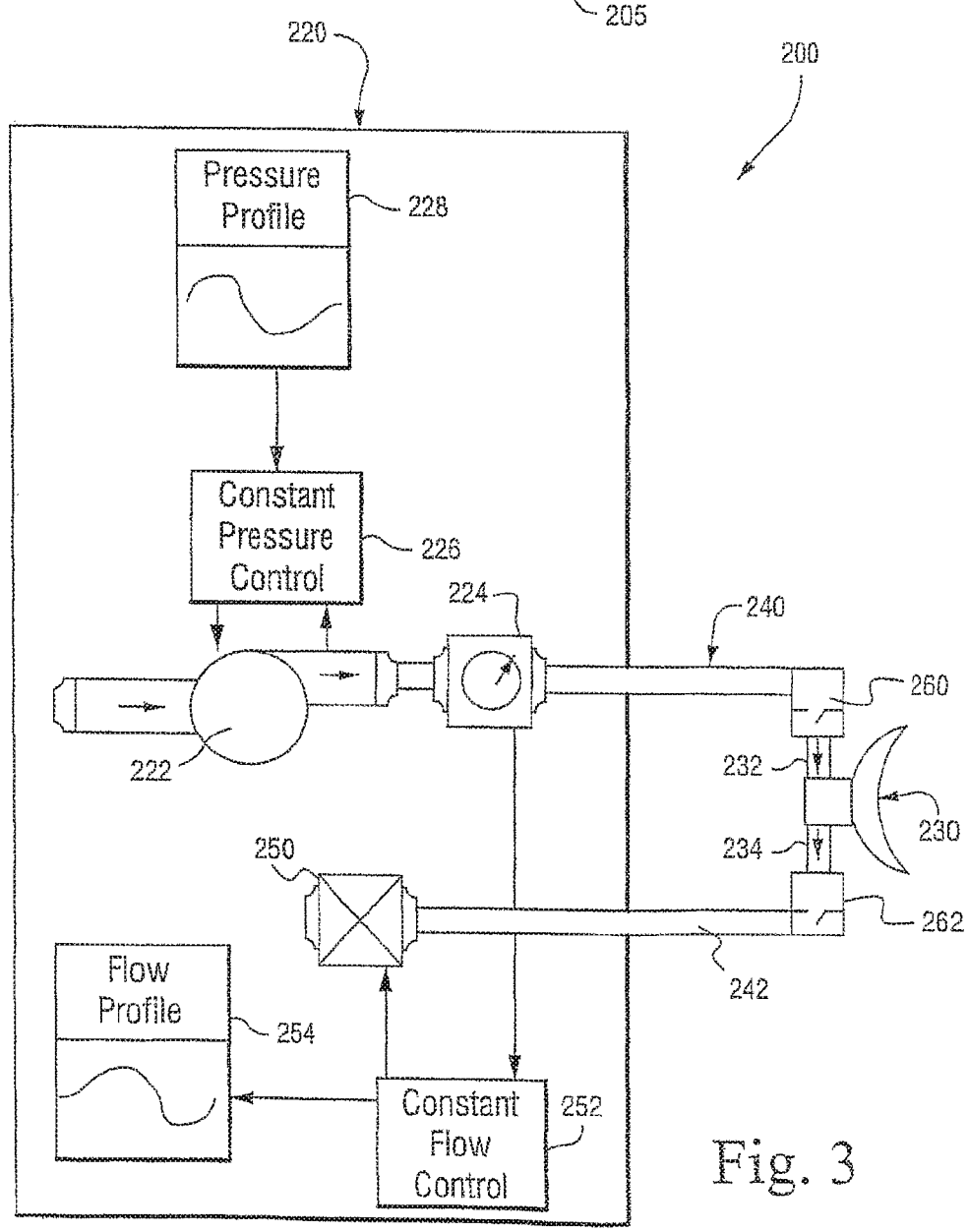
FIG. 3 is a schematic view of an air delivery system according to another embodiment of the present invention.

FIG. 3 illustrates an air delivery system 200 according to another embodiment of the present invention. Similar to the air delivery system 10, the air delivery system 200 includes an air flow generator 220, a patient interface 230, e.g., mask, and an air delivery conduit 240. The flow generator 220 includes an air turbine 222 controllably driven by a constant pressure control 226, and a flow measuring element 224. The patient interface or mask 230 is equipped with inlet and outlet ports 232, 234. A vent valve 250 is controlled by a constant flow control 252 to control the vent flow from the outlet port 234.

The air delivery system 200 includes several enhancements or variations with respect to the air delivery system 10. For example, one enhancement is that the vent valve 250 is physically located in the flow generator 220. Such an arrangement may be advantageous in simplifying the control of the vent flow and isolating any mechanical noise associated with the vent valve 250 from the patient. In order to locate the vent valve 250 within the flow generator 220, a return vent conduit 242 is provided between the vent valve 250 and the outlet port 234. Pressure regulation at the patient interface 230 may be retained if the pressure drop across the return vent conduit 242, and the vent valve 250 at maximum vent flow does not exceed the minimum mask pressure. If the pressure drop across the return circuit cannot be reduced sufficiently to maintain pressure regulation, then a partial vacuum may be applied to the exhaust port of the vent valve 250. This will compensate for some of the pressure drop in the return circuit and allow pressure regulation to be restored.

Another enhancement is that the conduit connections to the patient interface 230 include one-way valves in order to prevent reverse air flow from the patient to the flow generator for the purpose of reducing cross-infection. Specifically, the inlet port 232 communicated with air delivery conduit 240 includes one-way valve 260 that ensures that exhaled air cannot enter the air delivery path. The outlet port 234 communicated with the return vent conduit 242 includes one-way valve 262 that ensures that inhaled air cannot be taken from the vent. In normal operation, the air flow will pass from the air delivery path to the vent. In abnormal respiratory flows (e.g., coughs and gasping), the air flow may momentarily result in a flow reversal in either conduit 240, 242. The one-way valves 260, 262 prevent such reverse air flows, thereby reducing the possibility of patient contamination entering the delivery air path. The constant flow out of the flow generator would tend to prevent reverse air flow from happening, i.e., there is very little chance of expired air entering the flow generator.

Yet another enhancement is that the mask pressure may be controlled, possibly in synchronism with the respiratory flow, for the purpose of assisting respiration, improving comfort, and/or adapting therapy. For example, a basic representation or flow profile 254 of the respiratory flow can be obtained from the flow control 252 associated with the vent valve 250. The fidelity of the respiratory flow representation may be improved by the addition of sensors, either measuring the pressure drop across the vent valve 250 or directly measuring the flow through the vent valve 250. The respiratory flow is derived from the vent flow after removing non-respiratory flow components ($F_{resp}=F_{delivery}-F_{vent}-F_{nonresp}$). The flow profile 254 from the position of the vent valve 250 may be used to determine the respiratory flow to trigger the pressure profile 228.

The mask pressure profile 228 may be varied by applying the required waveform (increased by the pressure loss in the air delivery conduit 240) as the turbine pressure control set point. Because the pressure loss in the air delivery conduit 240 is constant at constant flow, the mask pressure will faithfully follow any applied pressure profile 228.

2.1 Control Algorithm

The control algorithm for the air delivery system 200 of FIG. 3 is basically the same as the air delivery system 10 of FIG. 1 (see FIG. 2). As illustrated, the measured air flow is obtained from the flow measuring element 224 at step 201. A target air flow, i.e., constant air flow, is established at step 202, and the measured air flow is compared to the target air flow at step 203. If the measured air flow is above the target air flow, then the vent valve 250 is opened via control 252 at step 204. If the measured air flow is not above the target air flow, then the vent valve 250 is closed via control 52 at step 205. The process continues through operation of the air delivery system 200 to maintain constant flow.

3. Third Illustrated Embodiment of Air Delivery System

Figure 4:
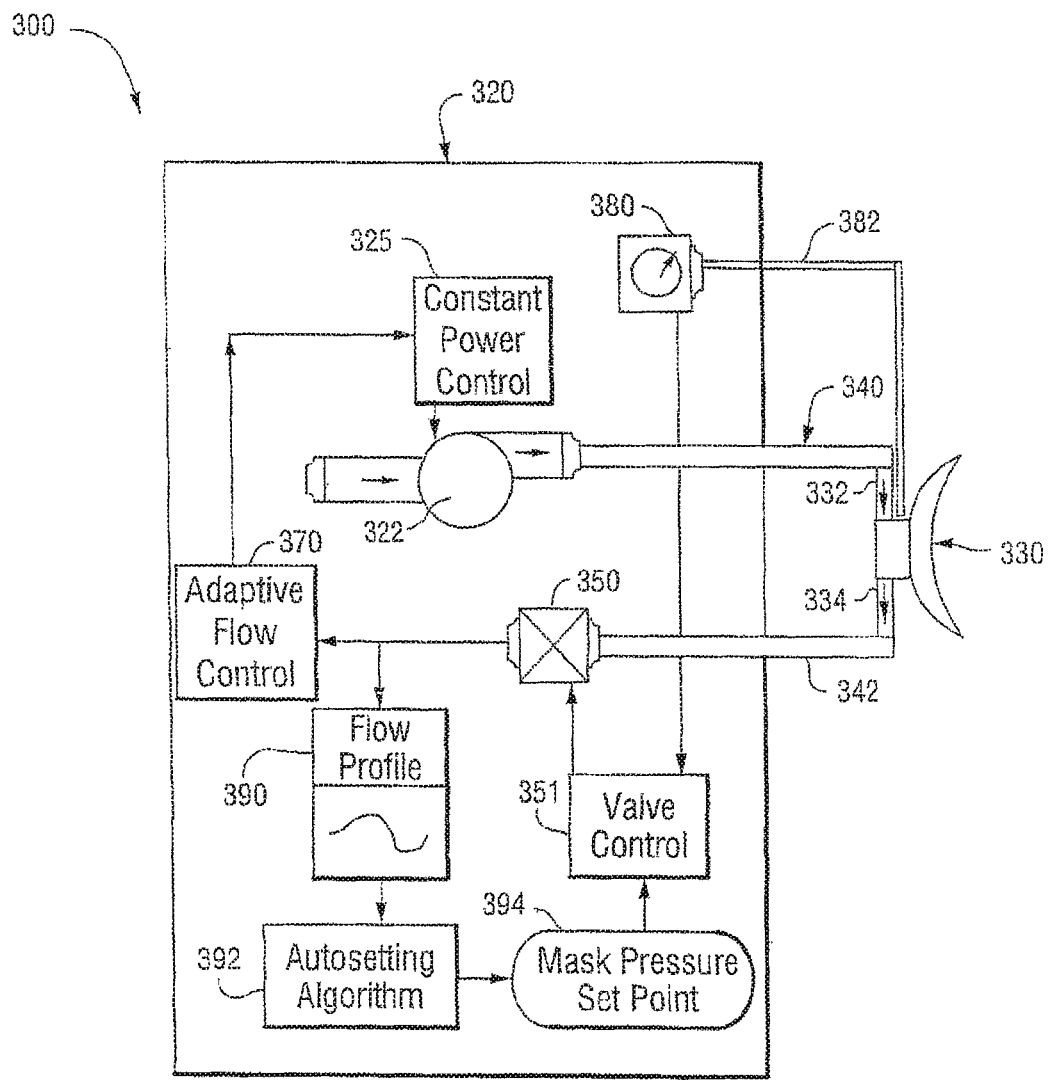
FIG. 4 is a schematic view of an air delivery system according to yet another embodiment of the present invention.

FIG. 4 illustrates an air delivery system 300 according to yet another embodiment of the present invention. As illustrated, the air delivery system 300 includes an air flow generator 320, a patient interface 330, e.g., mask, and an air delivery conduit 340.

The flow generator 320 includes an air turbine 322 that is set to operate at a specified power input by a constant power control 325. Alternatively, the air turbine 322 may be operated by a constant rpm or constant pressure controller. The air delivery conduit 340 includes one end communicated to the outlet of the flow generator 320 and an opposite end communicated to the inlet port 332 of the patient interface 330. A vent or exhaust valve 350 is preferably physically located in the flow generator 320, and a return vent conduit 342 is provided between the vent valve 350 and the outlet port 334 of the patient interface 330. The vent valve 350 is controlled by a valve control 351 to control the vent flow from the outlet port 334. In use, the valve control 351 adjusts the vent valve 350 so as to maintain constant pressure at the patient interface 330 (this will alter the flow in the air delivery circuit). Alternatively, a constant rpm or constant pressure controller may maintain constant pressure at the patient interface 330.

3.1 Adaptive Flow

As illustrated, an adaptive flow control 370 monitors the setting of the vent valve 350 and adjusts the specified power input at the constant power control 325 as required to minimize the air flow. That is, the 'constant' air flow in the air delivery circuit may be adjusted gradually by the adaptive flow control 370 so as to establish a Minimum consistent with the delivery of therapy. This optimization of the air flow is termed "adaptive flow." The operating limits of the vent valve 350 are monitored over time and the air delivery flow may be adjusted by changing the turbine pressure as shown below:

| Vent Valve Position | Air Delivery Flow | Adaptive Action |
|---|---|---|
| Often fully open | Too high | Reduce turbine pressure or power or rpm |
| Often fully closed | Too low | Increase turbine pressure or power or rpm |

Optimization of the air flow has several advantages. For example, reduction in average air flow reduces power consumption of the air turbine and reduces noise. Also, the operating range of the vent valve is maintained ensuring maximum control resolution. In addition, operating lifetime of the system may be increased.

When implemented, the vent valve 350 should not be fully closed (in a system with no fixed mask leak) as a minimum vent or exhaust flow will be needed to ensure mask $CO_2$ flush-out.

3.2 Introduction of Pressure Sensing at Mask

The pressure at the patient interface 330, e.g., mask, may be sensed directly at the patient interface 330. Pressure sensing at the patient interface 330 may be implemented through a pressure sensor mounted on or adjacent to the patient interface 330 (possibly in conjunction with a controllable vent valve) or a pressure sensor located in the flow generator and communicated with the patient interface via a pressure sensing tube.

In the illustrated embodiment, the pressure sensor 380 is located in the flow generator 320, and a pressure sensing tube 382 is provided between the pressure sensor 380 and the patient interface 330. In use, the pressure at the patient interface 330 may be monitored remotely by the pressure sensor 380 through the pressure sensing tube 382.

Other sensing arrangements for sensing pressure at the patient interface are described in U.S. Patent Application No. 60/731,483, entitled "Sensing Cuff for Breathing Apparatus," filed Oct. 31, 2005, the entirety incorporated herein by reference.

In previous embodiments, mask pressure is computed as a function of measured air flow and measured or computed turbine pressure. Pressure sensing at the patient interface removes the need for this computation.

Pressure sensing at the patient interface has several advantages. For example, air flow measurement does not need to be calibrated. The only indication of air flow needed is that sufficient to maintain the air flow constant. Also, operation is not affected by changes in impedance of the air delivery path, such as changes to patient circuit components or the gradual change in impedance of a humidifier.

3.3 Establishing 'Constant' Air Flow Delivery

Air delivery flow may be set without reference to a measured flow value. If impedance in the air delivery path remains constant, then maintaining a constant turbine rpm or turbine energy input will result in constant air flow. This is advantageous as it eliminates the need for an air flow sensing element.

In the absence of a calibrated air flow measurement, the autosetting flow algorithm (described below) would require the establishment of an initial condition from which it would then monitor vent valve position and optimize the air flow. In an embodiment, the pulse-width modulation (PWM) or energy input to the air turbine may be set relatively high to ensure that therapeutic mask pressure is available.

3.4 Fixed Flow Turbine Design

A fixed flow turbine design allows optimization of the air turbine for noise reduction and/or size reduction. If the air turbine rpm remains constant, then noise components due to rpm shift are eliminated. Even if a variable flow is implemented (e.g., as in adaptive flow described above), then the air turbine may be optimized for the air flow with zero mask leak as this would be the normal operating condition.

Prior art systems often require rising fan curve turbine designs (i.e., turbines that deliver higher pressure as the flow increases, at an essentially fixed rpm). According to an aspect of the present invention; keeping flow constant (or nearly constant) removes this constraint from the turbine design. Allowing, for example, fan curves that "fall" (i.e., that give far less pressure with increasing flow, at a fixed rpm) lead to flexibility in the turbine design, such that the turbine can be optimized for low noise and/or small size.

3.5 Mask Diffuser

In an embodiment, the patient interface or mask may have a diffuser, in addition to the inlet and outlet ports. The diffuser may be set to generate a required exhaust flow at 3 cm. As the mask pressure increases, a significant flow occurs through the diffuser in alternative designs. This flow is waste flow that has an energy cost. Each of the above-described embodiments are characterized by a controlled minimum flow that does not increase with increased mask pressure, which is an advantage. If the mask has a diffuser and the mask pressure varies, then the diffuser flow varies. This is an advantage of not having a diffuser in this design, i.e., the vent valve may be used to set a minimum flow out of the mask to ensure good $CO_2$ washout.

3.6 Delivery of Autosetting Pressure Therapy

In the illustrated embodiment, the setting of the vent valve 350 may be filtered to remove any DC component (representing mask leak). The resulting patient flow profiles may be used by an autosetting algorithm to adjust the mask pressure.

Specifically, a basic representation or flow profile 390 of the respiratory flow can be obtained by the filtered setting or position of the vent valve 350. The flow profile 390 may be used as an input to an autosetting algorithm 392. The autosetting algorithm 392 adjusts the mask pressure set point 394 via the valve control 351.

Examples of autosetting algorithms for delivering autosetting therapy (e.g., auto-titration) are described in U.S. Pat. Nos. 5,704,345 and 6,363,933, each of which is incorporated herein by reference in its entirety.

This arrangement provides a mechanism to deliver autosetting therapy without a flow sensor.

3.7 Measurement of True Leak and Patient Flow

The air flow in the air delivery conduit 340 and the return vent conduit 342 may be determined by pressure sensors. By placing a pressure sensor at each of the flow generator, the patient interface, and before the vent valve, the air flow in each conduit 340, 342 may be determined from a knowledge of the impedance of the air flow path. That is, subtracting the exhaust air flow from the delivery air flow yields the instantaneous patient air flow. A low pass filter of the patient air flow provides the mask leak.

3.8 Impact on Humidification

The air delivery systems described above may simplify humidifier design because the constant air flow yields more consistent humidification. That is, the reduction in air flow that arises out of the adaptive flow control and the removal of diffuser leak means that the humidification burden may be reduced, particularly at high pressures.

3.9 Control Algorithm

Figure 5:
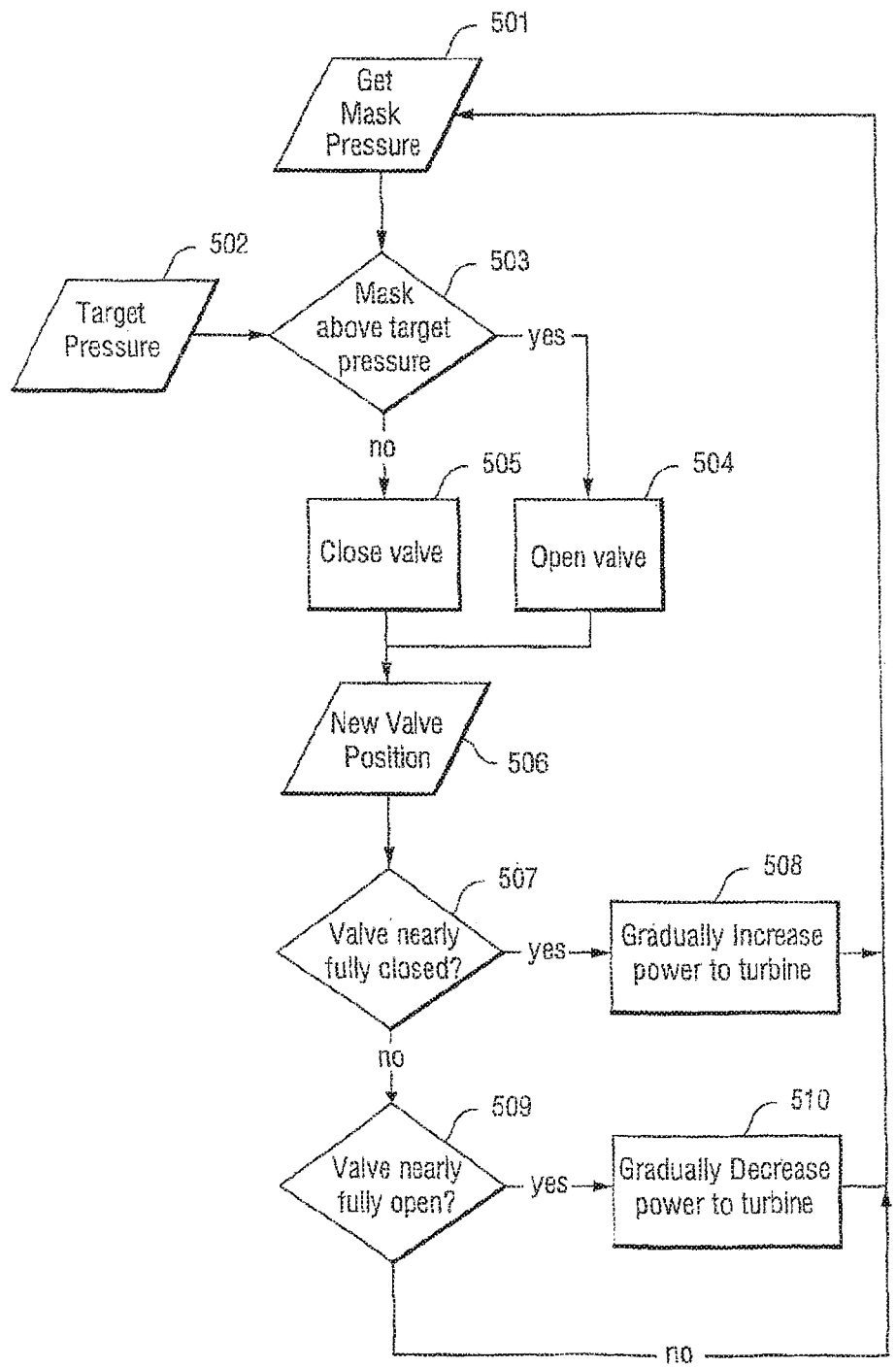
FIG. 5 is an embodiment of a control algorithm for the air delivery system shown in FIG. 4.

FIG. 5 illustrates a control algorithm for the air delivery system 300 of FIG. 4. The algorithm is preferably implemented using software, although hardware implementations are also possible. As illustrated, the patient interface pressure or mask pressure is obtained from the pressure sensor 380 at step 501. A target pressure, i.e., the mask pressure set point 394, is established at step 502, and the measured mask pressure is compared to the target pressure at step 503. If the mask pressure is above the target pressure, i.e., above the mask pressure set point 394, then the vent valve 350 is opened further via valve control 351 at step 504. If the mask pressure is not above the target pressure, i.e., not above the mask pressure set point 394, then the vent valve 350 is adjusted towards the closed position via valve control 351 at step 505. A new valve position is established at step 506.

If the new position of the vent valve 350 is nearly fully closed at step 507, then the power to the air turbine 322 is gradually increased via adaptive flow control 370 at step 508. If the new position of the vent valve 350 is nearly fully open at step 509, then the power to the air turbine 322 is gradually decreased via adaptive flow control 370 at step 510. If the new position of the vent valve 350 is neither nearly fully closed or open, then the process returns to obtaining the mask pressure at step 501. The process continues through operation of the air delivery system 300 to maintain constant flow.

4. Advantages

The air delivery systems described above may have specific advantages to the patient, physician, and/or manufacturer.

One advantage is that the air delivery systems described above may provide a system that is more comfortable and easier to use for the patient. For example, the relaxation of restrictions on delivery circuit resistance allows a more flexible design approach to the delivery/vent conduits. Also, because the air flow through any humidifier in the air delivery circuit is constant, the temperature and humidity of the air will not be affected by patient breathing. This uniformity may have benefits that outweigh the extra humidification required because the average air flow through the humidifier is higher.

Another advantage is that the air delivery systems described above may be easier to administer for the physician. For example, the constant flushing of the mask should result in lower levels of $CO_2$ and less rebreathing. With valves incorporated in the mask conduits, there would still be a flushing of clean air with the flow generator turned off. Further, the positive air flow through the flow generator reduces the possibility of patient contamination of the device. This arrangement may be an attractive alternative to disposable air paths in the flow generator.

Yet another advantage is that the air delivery systems described above may be cheaper for the manufacturer. For example, it may be cheaper to implement an air turbine and motor that does not require a low inertia and a humidifier that operates with a fixed air flow. Also, the relaxation of constraints on the delivery path resistance allows more cost effective approaches to noise reduction. Further, the reduction in motor rpm may increase the bearing lifetime and reduce operating temperatures.

Another advantage is that the control element of the system, i.e., vent valve, is in the exhaust path, so it does not come in contact with the patient air supply. This arrangement permits the use of alternative materials for the vent valve and sound absorbing. Further, the above-described systems do not require an accurately calibrated vent as part of the mask. In addition, the above-described systems prevent the use of competitor masks that do not have a second vent port.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

The invention claimed is:

1. A system for delivering pressurized air to a patient, the system comprising:
   a patient interface configured to communicate the pressurized air to the patient;
   an air source configured to deliver the pressurized air to the patient interface; and
   a vent valve configured to control venting from the patient interface to maintain a substantially constant pressure at the patient interface,
   wherein the patient interface is between the air source and the vent with respect to a direction of air flow from the air source to the vent.

2. The system according to claim 1, wherein the air source comprises an air flow generator.

3. The system according to claim 2, wherein the air flow generator includes a blower that is driven by a controllable electric motor.

4. The system according to claim 3, further comprising a constant pressure control configured to control the electric motor.

5. The system according to claim 4, wherein the constant pressure control includes a feedback circuit with a pressure transducer.

6. The system according to claim 3, further comprising a constant speed control configured to control the electric motor.

7. The system according to claim 2, wherein the air flow generator includes a flow measuring element to provide a representation of air flow through the air flow generator.

8. The system according to claim 2, wherein the vent valve is located external to the air flow generator.

9. The system according to claim 2, wherein the vent valve is located within the air flow generator.

10. The system according to claim 9, wherein the vent valve is communicated with the patient interface by a return vent conduit.

11. The system according to claim 1, wherein the vent valve is configured to vary flow rate through the vent valve to maintain the substantially constant pressure.

12. The system according to claim 11, wherein the system is configured to vary the flow rate through the vent valve as respiratory flow varies to maintain the substantially constant pressure.

13. The system according to claim 1, wherein the patient interface includes an inlet port communicated with an air delivery conduit for air delivery from the air source and an outlet port communicated with the vent valve for air venting.

14. The system according to claim 13, wherein the inlet port includes a one-way valve to prevent reverse air flow from the patient to the air source.

15. The system according to claim 1, further comprising a controller configured to calculate pressure at the patient interface as a function of measured air flow and measured or calculated pressure at the air source.

16. The system according to claim 1, wherein system is configured so that all $CO_2$ washout occurs through the vent valve.

17. A method for delivering pressurized air to a patient, the method comprising:
   delivering pressurized air to a patient interface from an air source; and
   using a vent downstream from the patient interface, controlling venting from the patient interface to maintain a substantially constant pressure at the patient interface while flow out of the vent is at or above a predetermined minimum flow rate.

18. The method of claim 17, wherein the air source is a flow generator, and further comprising controlling the flow generator to output a substantially constant pressure.

19. The method of claim 17, wherein the air source is a flow generator with an electric motor, and further comprising controlling the flow generator so that the electric motor operates at a substantially constant rpm.

20. The method of claim 17, wherein the air source is a flow generator, and further comprising controlling the flow generator to use substantially constant power to pressurize the air.

21. The method of claim 17, further comprising monitoring the venting and selectively controlling delivered air to establish a minimum air flow sufficient for CPAP therapy.

* * * * *